United States Patent [19]

Goyne et al.

[11] 4,223,921
[45] Sep. 23, 1980

[54] MOUNT FOR SUPPORTING A MEDICAL DEVICE

[75] Inventors: Thomas E. Goyne, Denver; Stephen J. Herman, Evergreen; Joel F. Giurtino, Littleton; Robert L. Anderson, Boulder, all of Colo.

[73] Assignee: Cobe Laboratories, Inc., Lakewood, Colo.

[21] Appl. No.: 918,360

[22] Filed: Jun. 23, 1978

[51] Int. Cl.² ............................................. F16L 35/00
[52] U.S. Cl. ....................................... 285/26; 285/61; 285/317; 248/542; 248/221.3; 128/DIG. 3; 422/46
[58] Field of Search .................. 248/542, 221.3, 222.1, 248/311.1 R; 128/DIG. 3; 422/45, 46, 47, 48; 285/61, 62, 63, 64, 325, 326, 317, 320, 137 R, 26, 29; 403/317, 327

[56] References Cited

U.S. PATENT DOCUMENTS

| 784,848 | 3/1905 | Fullipp | 285/325 X |
|---|---|---|---|
| 1,228,098 | 5/1917 | Cole | 248/311.1 X |
| 2,557,430 | 6/1951 | Hensley et al. | 248/311.1 X |
| 3,060,934 | 10/1962 | Claff et al. | 128/DIG. 3 |
| 3,332,746 | 7/1967 | Claff et al. | 128/DIG. 3 |
| 3,466,148 | 9/1969 | Everett | 422/46 X |
| 4,113,217 | 9/1978 | O'Connell | 248/221.3 |
| 4,116,476 | 9/1978 | Porter et al. | 285/137 R |

FOREIGN PATENT DOCUMENTS 244647  1/1966  Austria ..................................... 285/325

Primary Examiner—Dave W. Arola

[57] ABSTRACT

Sturdily mounting a disposable medical device by rotatably attaching a back plate to a back brace, biasing the back plate toward the medical device and employing a camming means on the back plate cooperating with a tab on the device to rotate the plate away from the device as the device is initially slid onto the mount and to return the plate to lock the device in place when the device is slid fully onto the mount.

8 Claims, 3 Drawing Figures

MOUNT FOR SUPPORTING A MEDICAL DEVICE

FIELD OF THE INVENTION

This invention relates to mounts for disposable medical devices.

BACKGROUND OF THE INVENTION

It is desirable to provide a mount for disposable medical devices that provides a positive locking means, simple installation and removal, and audible or tactile feedback to an operator to indicate that the device is securely and safely locked into the mount. Devices such as blood oxygenators with integral heat exchangers must be securely mounted to allow for connection of high pressure circulating heat exchange water and to support the load of blood and other fluids contained in them. Further, because these devices are generally discarded after use, it is desirable to be able to slide them quickly into and out of the mount.

SUMMARY OF THE INVENTION

We have discovered that a sturdy mount with a simple locking means can be provided for a disposable medical device by rotatably attaching a back plate to a back brace, biasing the back plate toward the medical device, and employing a camming means on the back plate with a first surface for cooperating with a tab on the medical device to rotate the back plate away from the device as the device is initially slid onto the mount and with a second surface for cooperating with the tab to return the back plate to a stop and lock the device in place when the device is slid fully onto the mount. In preferred embodiments, the mount features a ramp portion and groove defining the first and second surfaces of the camming means on the back plate; and a lever on the back plate for initiating backward movement of the device when removing it. Audible and tactile feedback is provided the operator when the device is locked in place, and the device is easily removed by rotating the backplate.

PREFERRED EMBODIMENT

The structure and operation of the preferred embodiment of the invention are as follows:

STRUCTURE

The drawings show the preferred embodiment and related apparatus, which are then described.

DRAWINGS

DESCRIPTION

Figure 1:
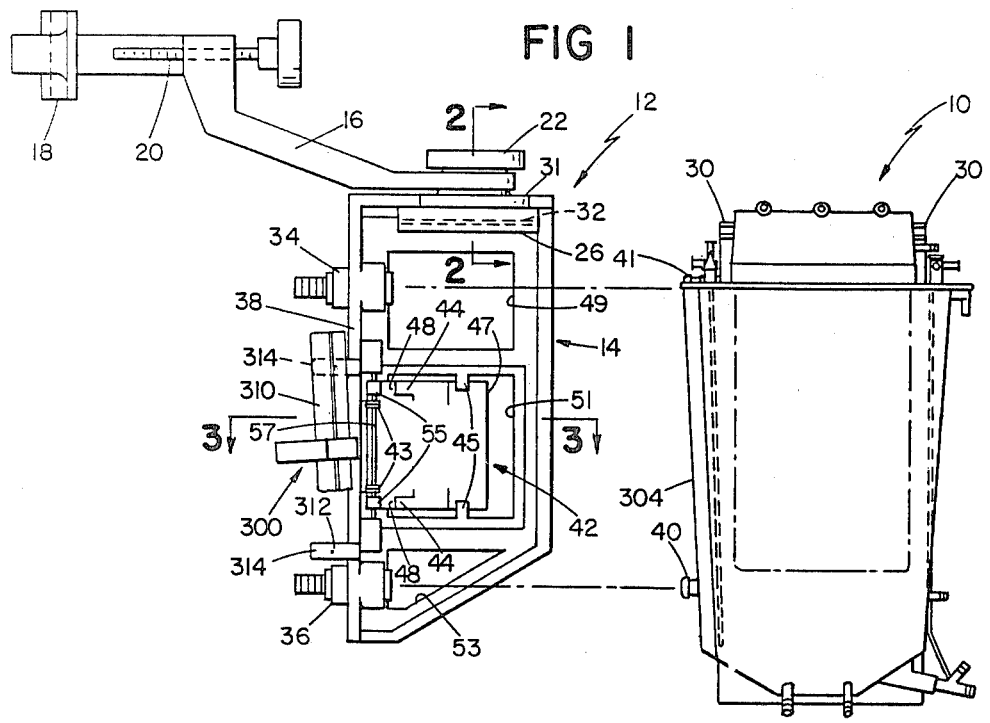
FIG. 1 is an elevation view of said embodiment, showing a blood oxygenator being inserted into its supporting mount (a portion of the mounting plate for a level monitor is cut away)

Turning to FIG. 1, there is shown blood oxygenator 10 being inserted into aluminum supporting mount 12. The mount has back brace 14 from which extends arm 16. At the end of arm 16 is formed V-shaped gripping portion 18 which cooperates with screw 20 to grasp a mounting post (not shown). Arm 16 is rotatably fastened to back brace 14 by nylon bearing 17 (FIG. 2), to which the arm is attached by two screws (not shown). Knob 22 turns screw 21 threaded into nylon bearing 17 to squeeze arm 16 and brace 14 against nylon lock washer 24 to lock the arm in any angular position in relation to the brace.

Below the arm-to-brace connection are nylon track portions 26, 28 (FIG. 2), which receive lip 30 on the top of oxygenator 10 and are secured to horizontal shelf 31 on brace 14. Track portion 26 has groove 32. Brass water couplings 34, 36 secured in vertical wall 38 by set screws (not shown) receive plastic inlet fitting 40 and outlet fitting 41 on oxygenator 10. Internal O-rings (not shown) in the brass couplings seal between the couplings and fittings. Back plate 42, which is biased by torsion springs 43 against stops 45 and and which has ramp portions 44 (FIG. 3), captures tab 46 on the back of oxygenator 10 in grooves 48 at the ends of the ramp portions. Openings 49, 51, 53 are provided in the brace. Back plate 42 swings through opening 51 into which stops 45 protrude. Level monitor mounting plate 310 fastened to bosses 314 by screws (not shown) received in holes 312 supports level monitor 300, which monitors the liquid level in oxygenator 10 by passing light through protruding ridge 304.

OPERATION

Figure 2:
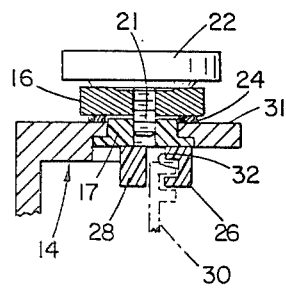
FIG. 2 is a fragmentary sectional view taken through 2—2 of FIG. 1.
Figure 3:
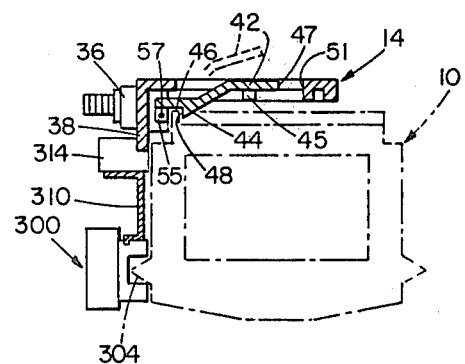
FIG. 3 is a fragmentary sectional view taken through 3—3 of FIG. 1 with the blood oxygenator shown installed in broken lines.

As depicted in FIGS. 1, 2, and 3, oxygenator 10 (a disposable unit) is installed in supporting mount 12 by inserting lip 30 formed as part of and along the top of the oxygenator into the track formed by track portions 26, 28 on mount 12. As the oxygenator is slid sideways, tab 46 protruding from the left rear corner of the oxygenator rides up on ramp portions 44, momentarily rotating back plate 42 backward (to the position shown by dashed lines in FIG. 3). The back plate snaps back into its normal position resting against stops 45 when tab 46 reaches and is received by groove 48, thereby locking the oxygenator in place. Removal of the oxygenator is accomplished by manually rotating back plate 42 backward by pulling on free end 47. Tabs 55 through which shaft 57 passes act as levers to provide disengagement forces when back plate 42 is rotated backward. These forces assist in overcoming any resistance imparted by the O-rings and couplings to fittings 40, 41 on the oxygenator. Water inlet and outlet fittings 40, 41 are received by and internally sealed to couplings 36, 34. Most of the vertical support for the oxygenator comes from the couplings, the remainder from track portion 26. Tubing (not shown) carrying temperature-controlled water is connected to water inlet fitting 40. Water output is carried away in tubing connected to water outlet fitting 41.

OTHER INVENTIONS

Subject matter disclosed herein relating to the level monitor was the joint invention of Donn D. Lobdell, Thomas E. Goyne, Stephen J. Herman, and Robert L. Anderson.

INCORPORATION BY REFERENCE

We incorporate by reference the copending U.S. patent application Ser. No. 917,350 of Donn D. Lobdell and Stephen J. Herman filed June 20, 1978 entitled "Gas Exchange Apparatus."

What is claimed is:

1. A mount for supporting a medical device, said mount comprising:
- a brace member for supporting a medical device placed alongside thereof,
- a horizontal track on said brace member for cooperating with a horizontal lip on said device to guide said device as it is slid onto said mount, said track defining an insertion direction,
- a back plate rotatably attached to a shaft which is attached to said brace member, whereby rotation of said back plate about the longitudinal axis of said shaft is allowed, said plate being rotatable away from said device from a locking position to an insertion position, said back plate including a gripping portion to allow manual rotation of said plate,
- means for biasing said back plate toward said medical device, said means being operably attached to said back plate,
- a stop member attached to said brace member for stopping rotation of said back plate toward said medical device beyond said locking position, and
- camming means on said back plate including
  - a first surface inclined with respect to said insertion direction when said back plate is in said locking position for cooperating with a tab on said medical device to rotate said back plate away from said device into said insertion position as said device is slid onto said mount and
  - a second surface substantially perpendicular to said insertion direction when said back plate is in said locking position, said second surface cooperating with said tab to allow said biasing means to return said back plate to said locking position after said tab passes said first surface, thereby locking said device in place when said device is fully slid onto said mount.

2. The mount of claim 1 further comprising a tubular fluid coupling for receiving internally a tubular fitting extending from said device and for providing support for said device when said device is slid onto said mount.

3. The mount of claim 1 wherein said first surface is the inclined surface of a ramp portion on said backplate and the second surface includes the inner wall of a groove in said ramp portion.

4. The mount of claim 1 wherein said back plate is rotatable about a vertical axis.

5. The mount of claim 1 wherein said means for biasing said back plate toward said medical device causes said back plate to snappably engage said tab when said device is fully slid onto said mount.

6. The mount of claim 1 wherein said back plate further comprises a lever for acting against said tab to initiate movement of said device out of said mount when said back plate is rotated away from said device.

7. The mount of claim 6 wherein said mount further comprises a tubular fluid coupling for receiving a tubular fitting extending from said device, said coupling having an internal O-ring for sealing between said coupling and said fitting and said lever providing enough force to overcome the resistance said O-ring and coupling impart when removing said device from said mount.

8. The mount of claim 1 wherein said horizontal track has a horizontal grooved portion for engaging said lip of said medical device and thereby providing added support for said device.

* * * * *